United States Patent [19]
Hjertman

[11] Patent Number: 5,810,778
[45] Date of Patent: Sep. 22, 1998

[54] APPARATUS FOR CONTROLLED DELIVERY OF LIQUIDS

[75] Inventor: Birger Hjertman, Hässleby, Sweden

[73] Assignee: Pharmacia & Upjohn Aktiebolag, Stockholm, Sweden

[21] Appl. No.: 564,181

[22] PCT Filed: Jun. 14, 1994

[86] PCT No.: PCT/SE94/00585

§ 371 Date: Feb. 21, 1996

§ 102(e) Date: Feb. 21, 1996

[87] PCT Pub. No.: WO95/00193

PCT Pub. Date: Jan. 5, 1995

[30] Foreign Application Priority Data

Jun. 18, 1993 [SE] Sweden ................................. 9302121

[51] Int. Cl.$^6$ .................................................. A61M 37/00
[52] U.S. Cl. .......................................... 604/143; 604/246
[58] Field of Search .................................... 222/386, 309, 222/340; 604/143–140, 246–224, 207, 208, 211, 209

[56] References Cited

U.S. PATENT DOCUMENTS 4,744,786  5/1988  Hooven ................................... 604/246

Primary Examiner—Phillipe Derakshani
Attorney, Agent, or Firm—Pollock, Vande Sande & Priddy

[57] ABSTRACT

An apparatus for a controlled delivery of a liquid preparation from a cylindrical liquid container, which has a liquid outlet at its front end and a movable wall, which acts like a piston at its rear end is provided. The driving force acting on the movable wall for expelling the liquid from the container is generated by means of a piston rod in connection with a piston, which by the action of the atmospheric pressure is urged into a space where a vacuum has been established. The amount delivered can be varied according to different modes by providing an auxiliary force which acts on the piston during the initial stage of its movement into the vacuum space.

20 Claims, 6 Drawing Sheets

APPARATUS FOR CONTROLLED DELIVERY OF LIQUIDS

TECHNICAL FIELD

The present invention refers to an apparatus for a controlled delivery of liquids. More specifically, the invention refers to an apparatus for such a delivery which may be varied during the time of delivery. Still more specifically, the invention refers to an apparatus for such a delivery of a pharmaceutical preparation by parenteral injection or infusion. Especially, the invention refers to such an apparatus which is independent of any external power source for its function.

BACKGROUND OF THE INVENTION

Devices for a controlled delivery of liquids, especially by parenteral injection or infusion, are previously known. Such devices are used when it is desired to administer a liquid preparation to a patient for an extended period of time. The preparation is expelled from a suitable container by some suitable driving force, and the delivery is controlled by arranging a suitable constriction in the conduit or line from the container to the patient receiving the administered liquid.

There are no problems in arranging this controlled delivery in a hospital where the driving force may simply be the hydrostatic head achieved by hanging up the container in an infusion stand of a well-known type. Furthermore, a number of infusion pumps are known, which are dependent on an external power source, such as electricity or compressed air. These pumps may also be programmed to give a delivery which can be varied with the time.

However, difficulties arise when a controlled infusion or injection is to be administered for an extended time where hospital facilities are not available, such as in the ambulatory treatment of accidents or sudden illnesses, such as heart attacks. For instance, in the treatment of a heart infarct, an administration of an antithrombotic agent, such as streptokinase, will often have to be given for an extended time of about an hour or more, where no programmed infusion pumps depending on an external power source are available.

There have been developed devices for administering parenteral injections or infusions for an extended period of time, which are not dependent on any external power source for driving an infusion pump. In one suitable embodiment of such devices, a vacuum is established in a chamber which is provided with a movable piston. The atmospheric pressure on the opposite side of the piston strives to move the piston into the vauum chamber, and through a suitable mechanical connection, such as a piston rod, this movement actuates a piston in an infusion pump or syringe to expel a preparation from said pump or syringe to administer it to a patient. The time for the administration is controlled by a suitable constriction in the flow path of the administered preparation.

Such devices have a number of important advantages. As the driving force is achieved by the atmospheric pressure acting against a vacuum, and not by any kind of gas-generating material, as is also previously known the force is constant over the time for administration. This means that a constant amount of the preparation is administered per unit of time. Furthermore, no gas-generating and potentially hazardous materials have to be handled. Also, in a specially preferred embodiment, the vacuum is established immediately before an infusion is administered. This eliminates the risk that the device becomes inoperative because of leaks having destroyed the pre-established vacuum.

Devices of the type mentioned above have been described in the international patent application No. PCT/SE91/00506, and have given good service. However, there is still room for improvement of these devices. As stated above, the amount of preparation administered per unit of time is essentially constant, because of the constant pressure acting on the piston against the vacuum. In certain applications, however, it is desired to administer a greater amount of preparation during an initial stage of the infusion, and a smaller, constant amount per unit of time during a later stage. One example of such an application is when agents are administered which initially are bound to the blood cells and are thus inactivated, and only later will act in their free form. Such is the case with tissue plasmin activator, TPA, for example. It may also be desired that said larger amount is constant per unit of time, or that it varies with time. These objects are achieved through the present invention.

SUMMARY OF INVENTION

According to the present invention, a device is provided for a controlled time-variable delivery of a liquid preparation from a cylindrical liquid container, which is provided at its front end with a liquid outlet having a constriction, and at its rear end is provided with a movable wall which functions like a piston to expel the liquid from said container through said outlet, said rear movable wall being urged forward by mechanical action by a force which is generated by the atmospheric pressure urging a first piston into first essentially empty vacuum space, and the invention is characterized in that auxiliary means are arranged to act on said movable wall in the liquid container by exerting a supplementary force on said first piston at an initial stage of its movement into said first vacuum space.

In a first embodiment of the invention, said auxiliary means is a pressure spring acting on said first piston against said vacuum space.

In a second embodiment of the invention, said auxiliary means is at least one auxiliary vacuum space, wherein the atmospheric pressure acts on at least one auxiliary piston, which is mechanically coupled to said first piston in said first vacuum space.

In a preferred embodiment of the invention, the device comprises two essential parts, a delivery unit which contains the preparation to be administered, and a power unit which contains the vacuum chamber and piston arrangement that supplies the driving force for the delivery. These two units are arranged to be coupled to each other coaxially, and when they are assembled together, the vacuum is established and the atmospheric pressure will start to exert its force on the piston. This force will, by means of a piston rod, be transferred to the piston in an infusion pump or syringe, to expel the liquid preparation.

In a still further preferred embodiment of the invention, the delivery unit is arranged as a holder for an injection cartridge of the single-chamber or dual-chamber type.

SUMMARY OF THE DRAWINGS

In the drawing,

FIGS. 5 and 6 show a device according to a second embodiment of the invention. In the description of the devices of the invention, the expressions "front" and "forward" signify the direction in which the liquid preparation is delivered from said device. Consequently, the expressions "rear" and "rearward" signify the opposite direction.

DESCRIPTION OF BEST AND VARIOUS MODES FOR CARRYING OUT INVENTION

Figure 1:
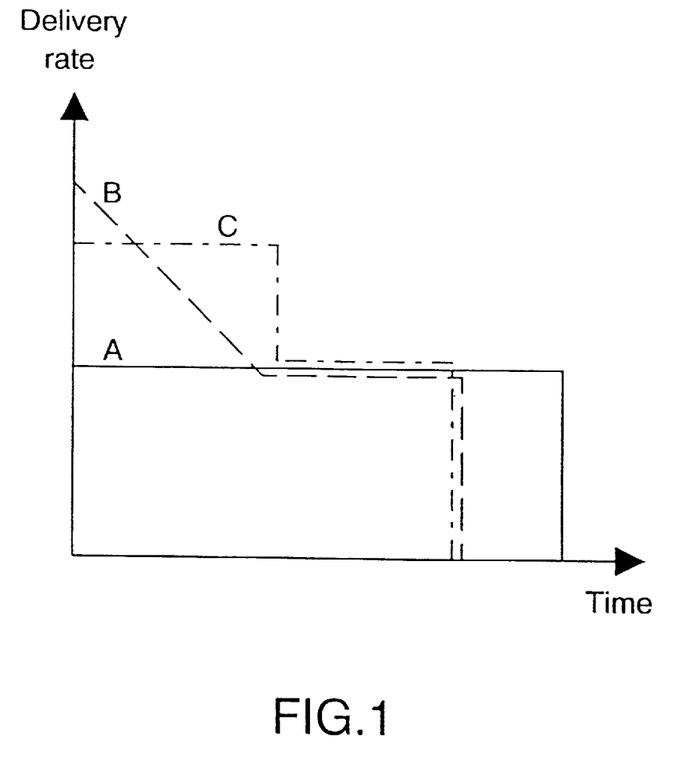
FIG. 1 is a diagram showing the various modes of delivery in accordance with the invention.

The diagram in FIG. 1 shows the delivery rate for the liquid preparation as a function of time. Graph A (full line) shows the delivery mode of the prior art. In this mode, the delivery rate remains constant from the beginning and decreases abruptly to zero when the vacuum source is depleted and the delivery is finished. Graph B (dashed line) shows the delivery mode according to a first embodiment of the invention. In this mode, the delivery rate is high at the beginning, and then decreases essentially in a linear manner until it approaches a determined value, where it remains constant until the delivery is finished. Graph C (dot-dashed line) shows the delivery mode according to a second embodiment of the invention. In this mode, the delivery starts at a high value and remains constant for a determined length of time, after which it drops abruptly to a lower value, where it remains constant during the remainder of the delivery. The various modes of delivery shown in the diagram can be arranged by means of the device of the invention.

Figure 2:
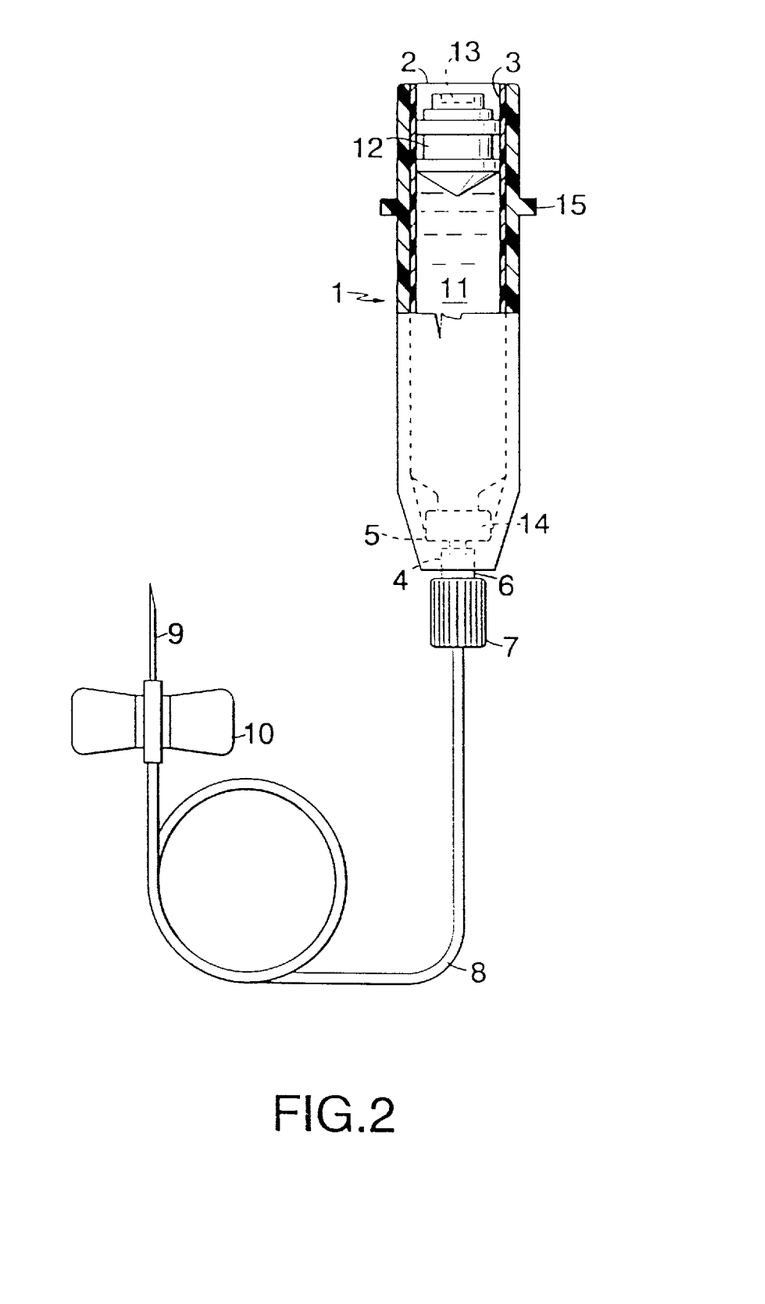
FIG. 2 shows a delivery unit of a device of the invention.

FIG. 2 shows a partly sectional view of a delivery unit of the apparatus of the invention.

The delivery unit comprises a sleeve 1, which has an opening 2, through which may be inserted an injection cartridge 3. At its other end, the sleeve 1 has a smaller opening 4 and an internal flange 5, against which the outlet end of the cartridge 3 rests. The smaller opening 4 is provided with a threaded connecting tube 6, onto which is screwed a threaded connecting piece 7. As shown in FIG. 1, this connecting piece 7 assures the connection between the smaller opening 4 of the sleeve 1 and a flexible tube 8, which at its other end is connected to a hypodermic needle 9. An adhesive tape 10 is provided for securing the needle assembly to the skin of the patient. It is of course also possible to connect the needle 9 directly to the connecting piece 7 without any intervening tube.

The injection cartridge 3 may be of a conventional construction. It contains a liquid 11 to be injected, and is closed at its rear end by a plunger or piston 12. This plunger may have a recess 13 at its rear end for receiving a connecting rod, as will be more closely explained hereinafter.

At its front end, the injection cartridge 3 is closed in a conventional way by a rubber septum which is held in place by a metal capsule 14. The connection between the cartridge 3 and the tube 8 via the connecting piece 7 also comprises a hollow needle (not shown), which in a known way pierces the rubber septum such that a liquid connection is established between the interior of the cartridge and the tube 8 with the needle 9.

In the drawing, the injection cartridge 3 is shown as a simple, single-chamber cartridge. However, it may also be a dual-chamber cartridge containing a dry active substance in one of the chambers and a liquid in the other, the two chambers being separated by a movable wall. Usually, the dry substance is in the front chamber and the liquid in the rear one. In the wall of the cartridge is arranged a bypass channel which may be operative or inoperative, depending on the position of the separating movable wall.

When the dual-chamber cartridge is to be made ready for use, the rear plunger is moved forward and will then also displace the liquid in the rear chamber forward. As the liquid is largely incompressible, it will in its turn urge the movable wall forward until it is such a position that the rear opening of the bypass channel is exposed to the liquid. The further movement of the rear plunger will then force the liquid through the bypass channel into the front chamber to dissolve the dry substance.

This arrangement is very suitable for the administering of substances which are too unstable to be stored in the form of a solution, such as certain hormones and proteins. In this way, the solution is not prepared until immediately before it is to be administered, and the mixing process can be made very carefully for delicate substances. The use of a dual-chamber cartridge is a preferred embodiment of the invention.

An important feature of the apparatus is that a flow restriction is arranged in the flow path of the liquid from the injection cartridge 3 to the hypodermic needle 9. This restriction may be arranged in the connecting piece 7 and may, for example, be a constriction, such as a capillary in the flow path of the liquid. The diameter of the constriction is adapted to the liquid to be injected such that a suitable flow is obtained. This adaption can be carried out by a person skilled in the art on the basis of simple routine tests.

The flow restriction may also be arranged in other ways. Thus, the tube 8 and/or the needle 9 for administering may themselves be of such dimensions that they act as a suitable restriction.

The flow restriction may also be adjustable, and may, for instance, be arranged as an adjustable clamp on the flexible tube 8.

The sleeve 1 is also provided with means for joining the delivery unit to the power unit shown in FIG. 2. These means may be arranged as a bayonet lock 15. Other arrangements for the joining are also possible, such as a snap joint or a threaded joint for screwing the two units together. It is important that the joint is secure, but yet can be released when desired.

Figure 3:
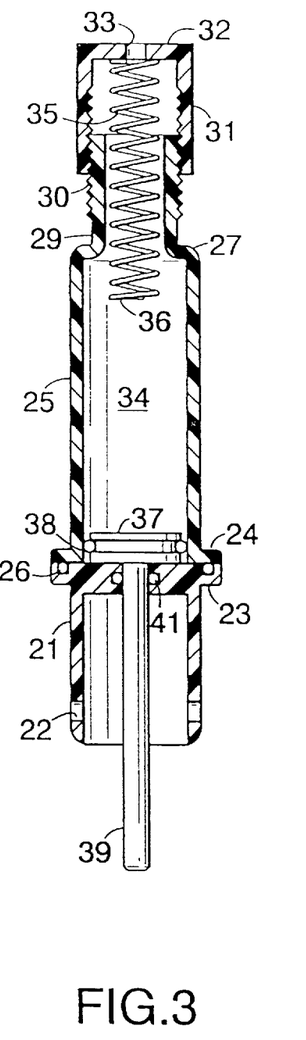
FIGS. 3 and 4 show an assembled device according to a first embodiment of the invention.

FIG. 3 is a sectional view of the power unit of an apparatus of the invention. This section comprises a sleeve 21 which is arranged to fit snugly over the rear part of the sleeve 1 of the delivery unit shown in FIG. 1. Means 22 are provided to cooperate with the means 15 (FIG. 1) to lock the two sleeves releasably together, such as by a bayonet lock.

The sleeve 21 is closed at its rear end by an end wall 23, which is shaped as a flange. To this flange is releasably attached the flange 24 of a cylinder 25. An airtight seal between the two flanges is assured by a sealing ring 26.

At its rear end, the cylinder 25 is provided with a shoulder 27, and is continued by a cylindrical coaxial portion 29 which has a smaller diameter than the cylinder 25. This rear portion 29 is provided with an external thread 30, on to which can be screwed an internally threaded cap 31. The cap 31 is closed at its rear end by a transversal wall 32, which has an aperture 33. Through this aperture 33, the internal space 34 in the cylinder 25 is in communication with the outside atmosphere.

Inside the threaded cap 31 and the cylindrical portion 29 is arranged a helical pressure spring 35 with its front end 36 protruding into the space 34 of the cylinder 25. The spring 35 is secured to the front face of the transversal wall 32 of the cap 31, and the distance which the front end 36 of the spring 35 protrudes into the space 34 can be regulated by screwing the threaded cap 31 more or less forward by means of the thread 30 on the cylindrical portion 29.

Inside the cylinder 25 is arranged a piston 37, which is in sealing contact with the interior wall of the cylinder via the sealing ring 38. In its resting postion, the piston rests on the rear surface of the end wall 23 of the sleeve 21.

To the front side of the piston is attached a piston rod 39, which sealingly traverses the end wall 23 through an orifice 40. An airtight seal between the piston rod 39 and the wall of the orifice 40 is assured by the sealing ring 41.

Thus, when the piston rod 39 and the piston 37 are moved rearward, there will be a vacuum established in the cylinder 25 in front of the piston 37, while the atmospheric pressure will prevail in the cylinder behind the piston, as this part of the cylinder is connected to the ambient atmosphere through the orifice 33.

Figure 4:
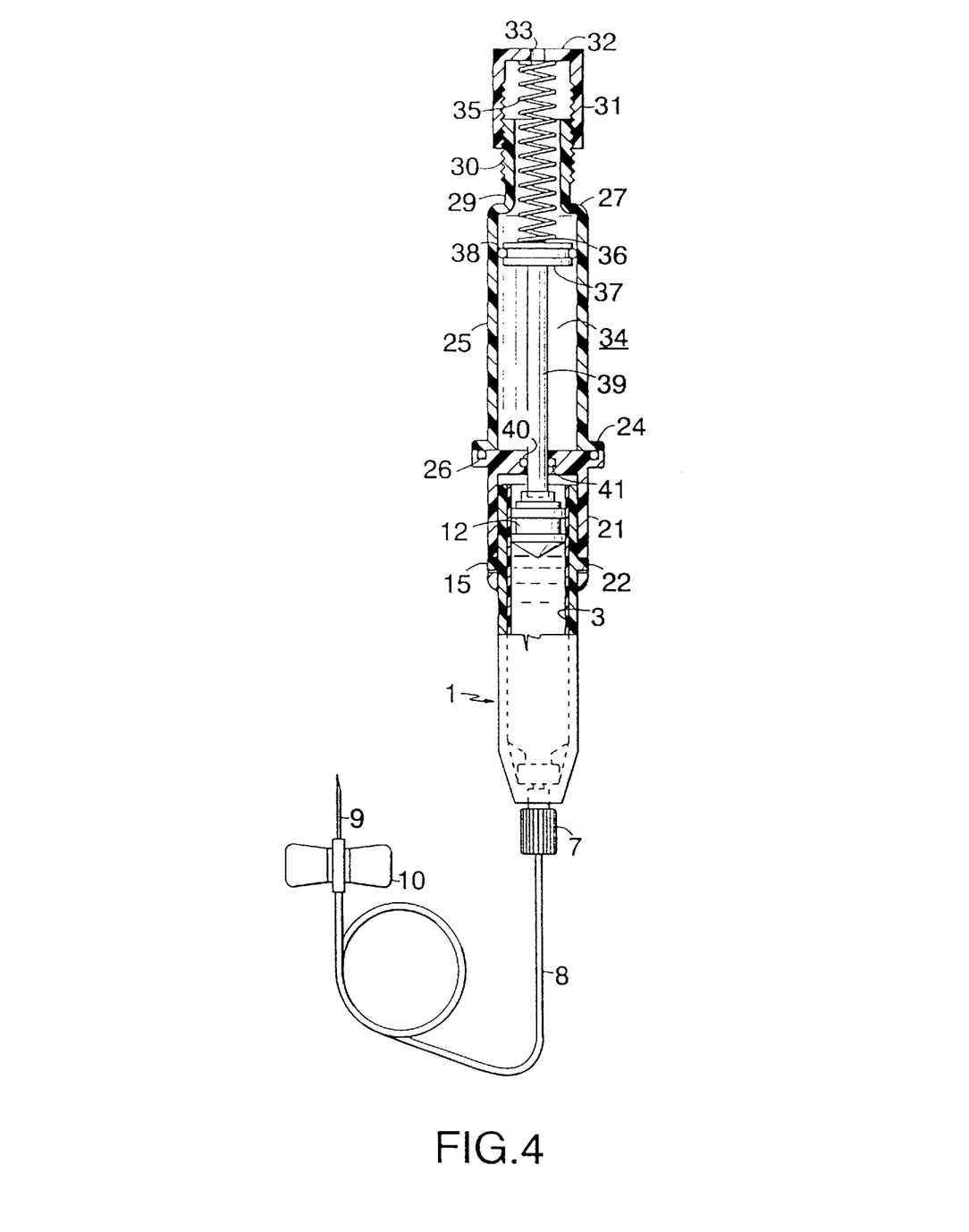

FIG. 4 shows the apparatus of the invention in an assembled state and ready for use. The sleeve 21 of the power unit has been placed around the rear part of the sleeve 1 of the delivery unit, and the two sleeves have been locked securely together by means of the bayonet lock 15, 22.

When the two sleeves 1, 21 are coaxially brought together, the forward end of the piston rod 39 will engage the recess 13 in the rear end face of the plunger 12 of the injection cartridge 3, to rest securely in said recess. The rod 39 and the piston 37 will then be moved rearward in the cylinder 25 as the two sleeves are brought together, so that a space will be established in the cylinder in front of the piston 29. Because of the seals made by the sealing rings 26, 38 and 41, no air can enter this space, so that a vacuum will be established therein. On the other side of the piston 37, the atmospheric air pressure acts on the piston, as the cylinder on this side is in connection with the ambient atmosphere through the orifice 33.

When the two sleeves 1, 21 have been locked together by means of the bayonet lock 15, 22, the piston 37 will be at its most rearward position in the cylinder 25. In the space in front of the piston in the cylinder, there will be a substantially complete vacuum, as the piston in its initial postion has rested on the end wall 23 of the sleeve 21, and there is essentially no space in front of it.

When the piston 37 is moved rearward through the assembly of the delivery unit and the power unit, its rear face will strike the front end 36 of the helical spring 35, and further rearward movement of the piston 37 will cause said helical spring to be compressed. The degree of compression of the spring may be regulated by screwing the threaded cap 31 more or less far onto the thread 30 of the cylindrical portion 29.

The atmospheric pressure will now act on the rear face of the piston 37 to force it forwards against the vacuum which has been established in the major part of the space 34 in the cylinder 25. Furthermore, the force of the compressed spring 35 will contribute to the force exerted by the atmospheric pressure. The combined force will be transmitted by the piston rod 38 to act on the rear face of the plunger 12 in the injection cartridge 3 to force the liquid 11 in the cartridge out through the tube 8 and the needle 9.

Figure 5:
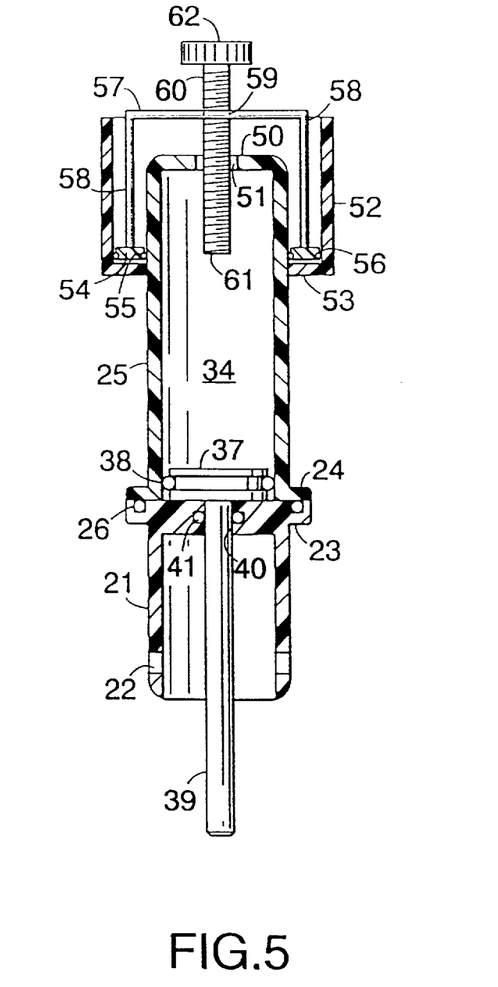

FIG. 5 shows another embodiment of the delivery unit of the apparatus of the invention. In this embodiment, the front part of the power unit is the same as shown in FIGS. 3 and 4, and it is intended to be connected to a delivery unit which is the same as that shown in FIG. 2. Thus, the power unit comprises a front sleeve 21 with means 22 for connecting it with the delivery unit, and a cylinder 25, in which is arranged sealingly a piston 37 having a piston rod 39, which sealingly traverses an aperture 40 in the end wall 23.

At its rear end, the cylinder 25 is terminated by a transversal wall 50, which has an opening 51. Through this opening 51, the internal space 34 of the cylinder 25 is in open connection with the ambient atmosphere.

Near its rear end, the cylinder 25 is surrounded by a second cylinder 52, which is coaxial with the first cylinder 25. This second cylinder 52 is connected to the first cylinder 25 by a shoulder part 53, and extends rearwards, usually— but not necessarily—for some distance beyond the rear end of the first cylinder 25. Thus, an annular space is formed between the outside of the first cylinder 25 and the inside of the second cylinder 52.

In this annular space is arranged an annular piston 54, which is sealed against the walls of the annular space by means of the sealing rings 55 and 56. The annular piston 54 is connected to a yoke 57. In the figure, this yoke 57 is shown having two arms 58 connected to the annular piston 54, but it goes without saying that the yoke may be provided with more than two arms.

The transversal part of the yoke 57 is provided with a threaded hole 59, wherein is arranged a screw 60. The hole 59 and the screw 60 are preferably coaxial with the first and second cylinders 25 and 52. The front end 61 of the screw 60 protrudes through the opening 51 into the space 34 of the cylinder 25 for a certain distance, which may be adjusted by rotating the screw 60 by means of the knurled head 62 at its rear end.

The annular piston 54 may be moved rearward in the annular cylinder 52 by moving the yoke 57. In its initial position, the annular piston 54 rests against the shoulder part 53 at the forward end of the second cylinder 52, and there is essentially no free space in front of said piston 54. Thus, when the annular piston 54 is displaced rearward, there will be established a vacuum in the space created in front of it, as it is sealed against the walls of the annular cylinder by means of the sealing rings 55 and 56. The rear face of the annular piston 54 is exposed to the ambient atmosphere, and thus the atmospheric pressure will strive to move the annular piston 54 forward against the vacuum in front of it.

Figure 6:
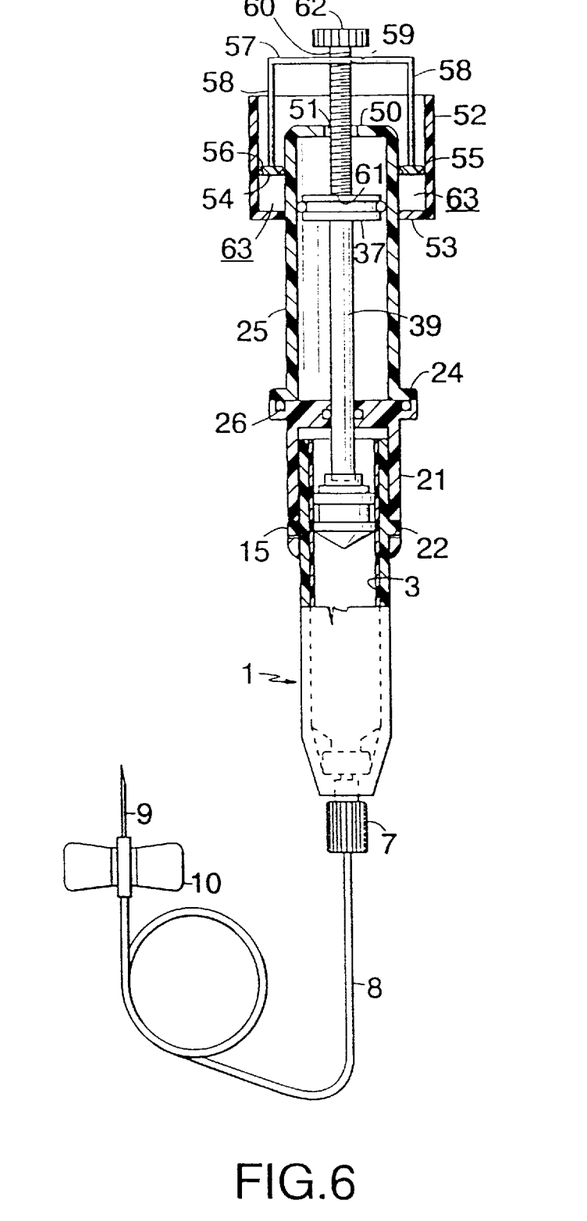

FIG. 6 shows the power unit of FIG. 5 connected to the delivery unit of FIG. 2. It will be seen that the connection arrangement between the delivery unit and the power unit is the same as has been described previously for FIG. 4. The difference between the two arrangements is apparent at the rear end of the power unit.

When the piston 37 is moved rearward by the assembly of the delivery unit and the power unit, its rear face will strike the front end 61 of the screw 60. Further rearward movement of the piston 37 will move the screw 60 and the yoke 57 rearward. As the annular piston 54 is connected to the yoke 57 by means of the arms 58, it will also be moved rearward in the annular cylinder, such that a vacuum is established in the space 63 of the annular cylinder. The distance that the annular piston 54 is moved rearward in the annular cylinder can be adjusted by turning the screw 60 by means of the knurled head 62.

The function of the apparatus of the invention is as follows:

When the apparatus is to be made ready for use, a fresh injection cartridge 3 is inserted into the sleeve 1 of the delivery unit, which is then connected to the power unit by means of the sleeve 21 and the locking means 15 and 22. When the two units are brought together, the front end of the piston rod 39 will engage the recess 13 in the rear face of the plunger 12 of the injection cartridge 3, and the piston 37 will be urged rearward in the cylinder 25. A vacuum will then be established in the cylinder 25 in front of the piston 37, and as the space of the cylinder behind the piston 37 is in connection with the ambient atmosphere, the atmospheric pressure will strive to move the piston 37 forward.

During the rearward travel of the piston 37 in the cylinder 25, the rear face of the piston will strike the front end 36 of the spring 35, as shown in FIG. 4, or the front end 61 of the screw 60, as shown in FIG. 6. Further rearward movement of the piston 37 will be against the added force of the spring 35 (FIG. 4), or against the additional force of the atmospheric pressure acting against the vacuum established in the annular cylinder space 63 (FIG. 6).

When a liquid preparation is to be administered from the injection cartridge 3, a liquid connection is opened at the front end of the cartridge by piercing its rubber septum with a hollow needle in connection with the connecting piece 7 and the tube 8. This liquid connection may also be established before the delivery unit and the power unit are joined to each other. The restriction in the flow path of the liquid is preferably closed at this stage.

When the restriction is opened to a suitable degree, the force acting on the piston 37 will be transmitted by the piston rod 39 to the plunger 12 of the injection cartridge 3, to urge said plunger forward and expel the liquid preparation from said cartridge. In the initial stage of the movement forward of the piston 37, an auxiliary force will act on it in addition to the force exerted by the atmospheric pressure on said piston 37. This auxiliary force will act in accordance with one of two embodiments of the invention:

In the first embodiment, shown in FIG. 4, the auxiliary force is exerted by a compressed spring. As the force exerted by a spring is proportional to its compression, this means that the auxiliary force is greatest when the spring is most compressed, and will decrease in an approximately linear manner as the compression decreases. Futhermore, the amount expelled from the injection cartridge per unit of time is approximately proportional to the force acting on the plunger 12. This means that in the initial stage of the administration, the amount administered will decrease in a substantially linear way with time.

When the piston 37 has traveled so far forward that its rear face is no longer in contact with the spring 35, the auxiliary force from said spring will end. During the further forward travel of the piston 37, it will only be driven forward by the atmospheric pressure acting against the vacuum in the cylinder 25 in front of said piston. This force is constant as long as there exists a vacuum, which means that the administered amount will also be constant with time.

The combined result of the two forces acting on the piston 37 in accordance with the first embodiment will then be an administering mode which is illustrated by graph B in FIG. 1. It will be seen that the administered amount is high at the beginning and then decreases in a linear manner uptil it reaches a constant value, which is maintained until the end of the administering.

In the second embodiment, shown in FIG. 6, the auxiliary force is exerted by the atmospheric pressure acting on the annular piston 54 in the annular cylinder between the first cylinder 25 and the second cylinder 52. This auxiliary force will remain constant as long as there exists a vacuum in front of the annular piston 54.

When the piston 37 has traveled so for forward that its rear face is no longer in contact with the front end 61 of the screw 60, the annular piston 54 will rest against the rear face of the shoulder part 53 of the second cylinder 52, and there will no longer exist any vacuum in front of said annular piston. This means that the auxiliary force will cease, and during the further forward travel of the piston 37, it will only be driven by the atmospheric pressure acting on its rear face. This force is also constant as long as there exists a vacuum in front of the piston 37.

The combined result of the two forces acting on the piston 37 in accordance with the second embodiment will be an administering mode which is illustrated by graph C in FIG. 1. It will be seen that as long as the atmospheric pressure acts on the annular piston 54 as well as on the piston 37, the administered amount remians at a constant high value. When the auxiliary force from the annular piston ceases, the administered amount decreases abruptly to a new value, which remains constant until the end of the administering In the apparatus according to the first embodiment of the invention, which is illustrated in FIGS. 3 and 4, the mode of administering may be adjusted by means of the threaded cap 31. The spring 35 is attached to the front face of the rear transversal wall 32 of the cap 31, and by screwing this cap onto the external thread 30 for a shorter or longer distance, it is possible to adjust the distance by which the front end 36 of the spring 35 protrudes into the cylinder 25. This distance determines for how much of the travel of the piston 37 that the spring 35 will exert its auxiliary force. The magnitude of this auxiliary force may be adjusted by selecting a spring 35 having a suitable stiffness. Thus, if the spring 35 protrudes into the cylinder 25 for a long distance, the initial auxiliary force will be higher, and it will take a longer time for it to decrease to zero, when the constant force on the piston 37 will prevail.

In the apparatus according to the second embodiment of the invention, which is illustrated in FIGS. 5 and 6, the mode of administrering may be adjusted by means of the screw 60, which is threaded through the cross part of the yoke 57. If the screw 60 is screwed through the yoke 57 far into the cylinder 25, the rear face of the piston 37 will strike the front end 61 of the screw 60 earlier on its travel rearward. This means that the annular piston 54 will be moved rearward a greater distance against the vacuum established in front of it. On the following forward movement of the piston 37, the auxiliary force exerted by the annular piston through the yoke 57 will therefore act for a longer time. In graph C in FIG. 1, the administering will then be made at the higher constant value for a longer time before it drops to the lower constant value. The magnitude of the auxiliary force in this embodiment is determined by the area of the annular piston 54 which is subjected to the atmospheric pressure.

It is to be noted that in the second embodiment of the invention, the second piston and cylinder assembly does not necessarily have to be arranged as an annular piston in an annular cylinder which encircles the first cylinder, as shown in FIGS. 5 and 6. Instead, the second cylinder may consist of an arrangement of a number of cylinders arranged along the exterior wall of the first cylinder, preferrably equidistantly, and having their axes essentially parallel with that of the first cylinder. In each of these second cylinders is then arranged a piston, and all these pistons are connected with a yoke, as shown in FIGS. 5 and 6. This arrangement will function in the same way as has been described in the foregoing, but its construction is somewhat more complicated.

In all other respects than the arrangement of the auxiliary force, the apparatus of the invention is arranged as is known from the prior art. Thus, the delivery unit is as described in the international patent application PCT/SE91/00506, and can comprise a single-chamber or a dual-chamber injection cartridge. The dual-chamber cartridge embodiment is preferred. In this case the preparation of the dual-chamber cartridge for injection in a manner known per se takes place in the initial stage of the assembling together of the delivery unit and the power unit. The rear piston of the cartridge will then be moved forward in the rear chamber of the cartridge to urge the front piston forward to expose the bypass channel and conduct the liquid from said rear chamber into the front chamber, to be mixed with the solid components therein. The design modifications which will be necessary are clearly apparent to persons skilled in the art.

It is an important feature of the apparatus of the invention that the delivery unit and the power unit are arranged along a common axis. In this way, the power unit will be actuated immediately when the two units are joined together, and the force of the piston will be transmitted in a linear direction from the power unit directly to the plunger in the delivery unit by means of the direct mechanical connection in the form of the piston rod.

The outflow of the liquid preparation from the delivery unit is controlled by a restriction in the flow path of the liquid, as described previously. This restriction may be constant and in the form of a capillary arranged in the flow path, or it may be variable and be arranged as a clamp on the outflow tube, for example. The flow path may be closed initially, and may then be gradually opened up when the administering starts.

The restriction is usually set such that the liquid in the cartridge will be administered for a time of at least about 30 minutes, and usually for an hour or more. However, these times are not critical to the invention, and may be set within very wide limits, from about a second up to 24 hours or more.

When the contents of the cartridge has been administered, the bayonet lock 15,22 is released and the two units are taken apart from each other. Under the influence of the atmospheric pressure, the piston 37 in the cylinder 25 of the power unit will then return to its foremost position. From the delivery unit, the injection cartridge 3 is removed through the rear opening 2, and is discarded. The connecting piece 7 is unscrewed from the connecting tube 6, so that the tube 8 with the hypodermic needle 9 at one of its ends and the connecting needle at its other end may be removed and discarded. A fresh cartridge may then be inserted into the sleeve 1 of the delivery unit, which may then again be connected with the power unit for a new administering. The liquid connection with the interior of the cartridge may be established before or after the delivery unit and the power unit have been connected together.

An advantage of the apparatus of the invention is tha the sleeve of the delivery unit and the complete power unit may be re-used an infinite number of times, and they do not have to be extensively sterilized, as they will not get into contact with the liquid preparation to be administered. The power unit with its auxiliary power units is not dependent on any external energy source, and the vacuum which constitutes its driving force is not established until immediately before the apparatus is to be used. This greatly diminishes the risks of possible leaks. Also, the driving and auxiliary forces are largely independent of variations in temperature. Both the delivery unit and the power unit are simple in their construction, and are therefore inexpensive to manufacture.

The choice of materials for the apparatus is not critical, and suitable materials may easily be selected by those skilled in the art. It is often desirable that the apparatus may be easily sterilized, for instance by autoclaving at en elevated temperature of at least about 120° C. Various plastic materials are suitable, and also metals, such as stainless steel and aluminum alloys.

In the foregoing, it has been pointed out that the use of an injection cartridge, especially of the dual-chamber type, is a preferred embodiment of the invention. However, this is not the only possible embodiment. It is also possible to use the sleeve 1 itself of the delivery unit as a container or syringe for the liquid preparation. For filling this container, the liquid is drawn up from a suitable liquid reservoir through a needle attached to the front end of the sleeve, by means of a suitably arranged plunger in the sleeve. After the container has been filled in this way, the further function of the apparatus is as described in the foregoing.

It is to be noted that the present invention is not limited to only the embodiments specifically shown in the drawings and described in the foregoing specification. To a person skilled in the art, other variants and modifications are possible without departing from the scope of the invention as defined by the appended claims.

I claim:

1. Apparatus for a controlled time-variable delivery of a liquid preparation from a cylindrical liquid container having at its front end a liquid outlet provided with a constriction, and at its rear end a movable wall, which functions like a piston to expel said liquid from said container through said outlet, said rear movable wall being urged forward by mechanical action by a force which is generated by the atmospheric pressure urging a first piston into a first essentially empty vacuum space, and characterized in that auxiliary means are arranged to act on said movable wall by exerting a supplementary force on said first piston at the initial stage of its movement into said first vacuum space.

2. Apparatus according to claim 1, characterized in that said auxiliary means is a pressure spring which acts on said first piston against said vacuum space.

3. Apparatus according to claim 1, characterized in that said auxiliary means comprise at least one auxiliary space wherein essentially a vacuum has been established and wherein the atmospheric pressure acts on at least one auxiliary piston, which is mechanically coupled to said first piston in said first vacuum space.

4. Apparatus according to claim 1, characterized in that it comprises a delivery unit, which contains the container for the liquid preparation, and a power unit, which comprises a first cylinder which contains said first vacuum space and said first piston, the two units being assembled coaxially such that at the assembling, said first piston has been urged rearward in said first cylinder by means of a piston rod such that said first vacuum space has been established in front of said first piston and the atmospheric pressure exerts a forward driving force on said first piston, this driving force acting on the movable wall of said container for the liquid preparation by means of said piston rod and striving to urge said movable wall forward, and that said auxiliary means are arranged near the rear end of said first cylinder to cooperate with the atmospheric pressure at the initial stage of the forward movement of said first piston.

5. Apparatus according to claim 4, characterized in that a pressure spring is arranged within said first cylinder on the rear side of said first piston in such a way that it exerts a forward directed pressure force on said first piston at the initial stage of its forward movement.

6. Apparatus according to claim 4, characterized in that near the rear end of the first cylinder is arranged at least one second cylinder wherein a second piston is arranged movable and mechanically coupled to said first piston in such a way that when said first piston is moved rearward, said second piston is also moved rearward, establishing a space with essentially a vacuum in said second cylinder.

7. Apparatus according to claim 6, characterized in that said second cylinder is arranged in annular arrangement around said first cylinder near its rear end, said second piston being annular and arranged movably in said second cylinder.

8. Apparatus according to claim 1, characterized in that a mechanism is arranged to adjust the distance which said first piston is acted on by said auxiliary means during its travel forward.

9. Apparatus according to claim 8, characterized in that said mechanism is a screw mechanism.

10. Apparatus according to claim 1, characterized in that said container for the liquid preparation is an injection cartridge having one or more chambers.

11. Apparatus according to claim 2, characterized in that it comprises a delivery unit, which contains the container for the liquid preparation, and a power unit, which comprises a first cylinder which contains said first vacuum space and said first piston, the two units being assembled coaxially such that at the assembling, said first piston has been urged rearward in said first cylinder by means of a piston rod such that said first vacuum space has been established in front of said first piston and the atmospheric pressure exerts a forward driving force on said first piston, this driving force acting on the movable wall of said container for the liquid preparation by means of said piston rod and striving to urge said movable wall forward, and that said auxiliary means are arranged near the rear end of said first cylinder to cooperate with the atmospheric pressure at the initial stage of the forward movement of said first piston.

12. Apparatus according to claim 3, characterized in that it comprises a delivery unit, which contains the container for the liquid preparation, and a power unit, which comprises a first cylinder which contains said first vacuum space and said first piston, the two units being assembled coaxially such that at the assembling, said first piston has been urged rearward in said first cylinder by means of a piston rod such that said first vacuum space has been established in front of said first piston and the atmospheric pressure exerts a forward driving force on said first piston, this driving force acting on the movable wall of said container for the liquid preparation by means of said piston rod and striving to urge said movable wall forward, and that said auxiliary means are arranged near the rear end of said first cylinder to cooperate with the atmospheric pressure at the initial stage of the forward movement of said first piston.

13. Apparatus according to claim 2, characterized in that a mechanism is arranged to adjust the distance which said first piston is acted on by said auxiliary means during its travel forward.

14. Apparatus according to claim 3, characterized in that a mechanism is arranged to adjust the distance which said first piston is acted on by said auxiliary means during its travel forward.

15. Apparatus according to claim 4, characterized in that a mechanism is arranged to adjust the distance which said first piston is acted on by said auxiliary means during its travel forward.

16. Apparatus according to claim 5, characterized in that a mechanism is arranged to adjust the distance which said first piston is acted on by said auxiliary means during its travel forward.

17. Apparatus according to claim 6, characterized in that a mechanism is arranged to adjust the distance which said first piston is acted on by said auxiliary means during its travel forward.

18. Apparatus according to claim 7, characterized in that a mechanism is arranged to adjust the distance which said first piston is acted on by said auxiliary means during its travel forward.

19. Apparatus according to claim 2, characterized in that said container for the liquid preparation is an injection cartridge having one or more chambers.

20. Apparatus according to claim 3, characterized in that said container for the liquid preparation is an injection cartridge having one or more chambers.

* * * * *